United States Patent [19]

Takeuchi et al.

[11] Patent Number: 4,465,830

[45] Date of Patent: Aug. 14, 1984

[54] LATENT CURING AGENTS FOR EPOXY RESINS

[75] Inventors: Koji Takeuchi, Yokohama; Nobuo Ito, Oisomachi; Masahiro Abe; Kiyomiki Hirai, both of Kawasaki, all of Japan

[73] Assignee: Ajinomoto Company, Incorporated, Tokyo, Japan

[21] Appl. No.: 537,328

[22] Filed: Oct. 3, 1983

Related U.S. Application Data

[63] Continuation of Ser. No. 445,154, Nov. 29, 1982, abandoned.

[30] Foreign Application Priority Data

Dec. 1, 1981 [JP] Japan ................................ 56-193065
Jan. 29, 1982 [JP] Japan ................................ 57-12892

[51] Int. Cl.³ .................... C08G 59/44; C08G 59/54; C07D 403/30
[52] U.S. Cl. .................... 528/117; 525/504; 528/365; 528/367; 548/312; 548/313
[58] Field of Search ................... 528/117, 365, 367; 525/504; 548/312, 313

[56] References Cited

U.S. PATENT DOCUMENTS

| | | | |
|---|---|---|---|
| 3,597,441 | 8/1971 | Wollner et al. | 548/312 |
| 3,635,844 | 1/1971 | Porret et al. | 528/117 |
| 3,635,845 | 1/1972 | Porret et al. | 528/117 |
| 3,725,342 | 4/1973 | Porret et al. | 528/117 X |

OTHER PUBLICATIONS

"Nippon Kagaku Zasshi" 83, No. 5, 620–624 (1962) with English Translation.

*Primary Examiner*—Earl A. Nielsen
*Attorney, Agent, or Firm*—Oblon, Fisher, Spivak, McClelland & Maier

[57] ABSTRACT

Hydrazides of the formula

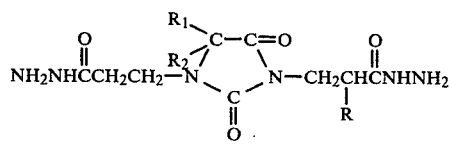

are good curing agents for epoxy resin, in the formula $R_1$ and $R_2$ being each hydrogen atom, $C_1$–$C_8$ alkyl radical or —$CH_2CH_2SCH_3$, R being hydrogen atom or methyl radical. The curing agents are useful in formulating novel storable one-package, heat-curable epoxy resins-based compositions.

12 Claims, No Drawings

LATENT CURING AGENTS FOR EPOXY RESINS

This application is a continuation of application Ser. No. 445,154, filed Nov. 29, 1982, now abandoned.

The present invention relates to certain novel hydrazides and the use thereof as curing agents for epoxy resins.

Epoxy resins are widely employed as electric insulating materials, various moulded products, adhesives or coatings, because they give valuable cured resins having excellent mechanical, electrical and chemical properties when cured with suitable curing agents for example acid anhydride and amine curing agents. However, epoxy resin compositions incorporating amine curing agents are cured rapidly at ordinary temperature and at elevated temperature and hence they lack storage stability. Also, epoxy resin compositions incorporating acid anhydride curing agents are stable at ordinary temperature but heating for a long period of time at elevated temperature is required for full curing. Usually, tertiary amines, quaternary ammonium compounds or organo metal complexes are further added to the composition for purpose of accelerating curing rate. However, the addition of such cure accelerator impairs storage stability markedly.

There have been eagerly desired so-called latent curing agents which are compatible with epoxy resins to form compositions which are stable at relatively low temperature and which is rapidly cured when heated to elevated temperature. Representative compounds which have been heretofore proposed as latent curing agents are dicyandiamide, dibasic acid hydrazide, boron trifluoride-amine adduct, guanamine and melamine. Among these compounds, dicyandiamide, dibasic acid hydrazide and guanamine are useful in formulating epoxy resin compositions having excellent storage stability but full curing by means of these compound could be achieved by heating at higher temperature than 150° C. for a long time. Also, boron trifluoride-amine adduct is hard to treat owing to its high hygroscopic property and it affects adversely upon the physical properties of the cured resin.

There has been heretofore known almost no latent epoxy curing agent which causes rapid curing at moderate elevated temperature, that is 100° C.-150° C. and which gives epoxy resin composition having excellent storage stability at ordinary temperature.

An object of the present invention is to provide novel hydrazide-type curing agents which are useful in making storable one-package curable epoxy resin compositions.

Another object of the present invention is to provide hydrazide-type curing agents which alone or together with other curing agents can activate a rapid curing of epoxy resin compositions at relatively low temperatures and yet be extraordinarily resistant to gelling at 40° C. for three weeks or more weeks.

The above objects of the present invention may be substantially achieved by providing as curing agent hydrazide compounds having the following general formula (I) or (II).

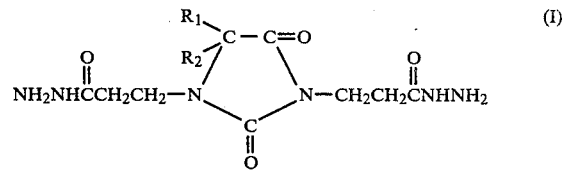

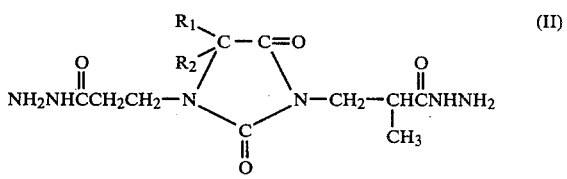

wherein $R_1$ and $R_2$ are each hydrogen atom or alkyl radical having 1 to 8 carbon atoms or $-CH_2-CH_2SCH_3$.

The hydrazides which may be represented by the above general formula (I) or (II) may be readily prepared by reacting adduct of 1 mole of hydantoin compound and 2 moles of acrylic ester $CH_2=CHCOOR'$ or adduct of equimolar proportions of hydantoin compound, acrylic ester and methacrylic ester

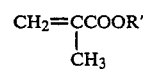

with hydrated hydrazine, said hydantoin compound being represented by the following general formula (a)

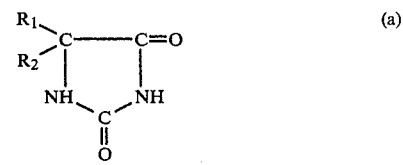

wherein $R_1$ and $R_2$ have the meanings set forth above, said adduct of hydantoin compound and bimolecular acrylic ester being represented by the following general formula (b)

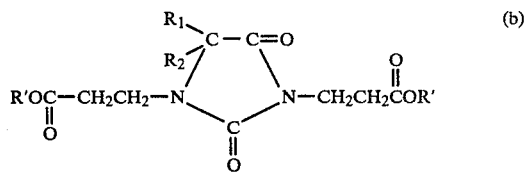

wherein $R_1$ and $R_2$ have meanings set forth above and R' is alkyl radical, and said adduct of equimolar proportions of hydantoin compound, acrylic ester and methacrylic ester being represented by the following general formula (c)

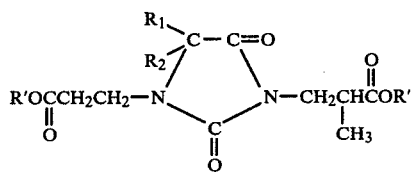

(c)

wherein $R_1$, $R_2$ and $R'$ have the meaning set forth above.

The preparation of the adduct (b) of hydantoin compound and bimolecular acrylic ester may be carried out by heating the hydantoin compound and an acrylic ester in the presence of a basic catalyst such as potassium hydroxide in the absence or presence of a solvent such as methanol and ethanol at reflux temperature for several hours, the amount of acrylic ester being at least twice as many moles as the hydantoin compound.

Also, the preparation of the adduct (c) of hydantoin, acrylic ester and methacrylic ester may be carried out by the following two stages of reaction. The hydantoin compound is first reacted with methacrylic ester in the presence of basic catalyst in the absence or presence of solvents such as methanol and ethanol at around 150° C. for several hours under pressure, the amount of methacrylic ester being at least 1 mole based on the hydantoin compound whereby the adduct of equimolar proportions of hydantoin compound and methacrylic ester is formed which may be represented by the general formula (c').

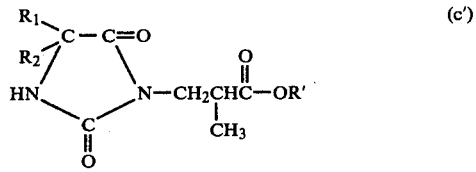

(c')

The hydantoin-methacrylic ester adduct (c') is separated from excess methacrylic ester at the completion of the reaction by distilling the remaining methacrylic ester under reduced pressure and then reacting (c') with acrylic ester in the presence of basic catalyst and in the absence or presence of the solvent at reflux temperature for several hours, whereby the desired adduct (c) is prepared.

The acrylic ester and/or methacrylic ester to be reacted with the hydantoin compound is not particularly limited. Usually a lower $C_1$–$C_4$ alkyl ester is employed. Especially methyl ester is practical. The amount of basic catalyst may be about 1% by weight based on the hydantoin compound. The addition reaction is usually carried out in the presence of a polymerization inhibitor for acrylic ester such as hydroquinone. After the additional reaction has been completed, excess acrylic ester and solvent if any are removed from the reaction mixture by distillation.

The hydantoin-acrylic ester adduct (b) or the hydantoin-acrylic ester-methacrylic ester adduct (c) so prepared is further reacted with hydrated hydrazine in the presence of solvent such as methanol or ethanol at the reflux temperature for several hours, the amount employed of hydrated hydrazide being at least twice as many moles as the adduct (b) or (c).

After the completion of the reaction, excess hydrated hydrazine and the solvent are removed from the reaction mixture by distillation and the precipitated hydrazide is separated and recrystallized from a suitable solvent such as methanol, ethanol or water. The hydrazide of the present invention may be pulverized in fine particles.

The hitherto known dibasic acid hydrazides such as adipic acid hydrazide, sebacic acid hydrazide, isophthalic acid hydrazide and the like are high melting compounds, melting above 180° C., and the epoxy resin compositions incorporating such dibasic acid hydrazides are cured when heated to 150° C. or higher temperatures. Contrary thereto, the hydrazides of the present invention are relatively low melting compounds and provide when incorporated into an epoxy resin, curable compositions which are stable for periods of several weeks at 40° C. and which can thereafter be readily cured at temperatures of as low as about 100° to 130° C. to give a colorless, transparent and tough cured product.

The required amount of curing agent is determined by the number of active hydrogen atoms in the curing agent employed and the number of epoxy groups in the epoxy resins. In general, 0.5–1.5 preferably 0.7–1.2 active hydrogen equivalent weight per epoxy equivalent weight is employed.

The substituents $R_1$ and $R_2$ in the general formula (a) of the hydantoin compound which is the starting material for preparing the latent curing agent of the present invention are each hydrogen, alkyl radical having 1 to 8 carbon atoms such as methyl, ethyl, propyl, isopropyl, butyl, sec.-butyl, amyl, hexyl and octyl; and —$CH_2CH_2SCH_3$. Representative examples of the hydantoin compounds include hydantoin, 5-methylhydantoin, 5-ethylhydantoin, 5-propylhydantoin, 5-isopropylhydantoin, 5-sec.-butylhydantoin, 5-octylhydantoin, 5,5-dimethylhydantoin, 5-methyl-5-ethylhydantoin and 5-[2-(methylthio)ethyl]hydantoin. Especially, hydrazides derived from the starting material 5-propylhydantoin, 5-isopropylhydantoin, 5-sec.-butylhydantoin and methioninehydantoin are the preferred curing agents because they provide when incorporated into epoxy resins, compositions which can be cured at temperatures of as low as 110° C.

As epoxy resins which may be applied to the hydrazide curing agents of the present invention, various well-known ones having an average of more than 1 epoxy groups in the molecule may be employed. Representative epoxy resins are those based on glycidyl ethers of polyhydric phenols such as 2,2-bis(4-hydroxyphenyl)-propane (Bisphenol A), resorcinol, hydroquinone, pyrocatechol, saligenin, glycidyl ether of Bisphenol F and glycidyl ether of phenolformaldehyde resin.

If necessary, other curing agents, cure accelerator and fillers may be employed in combination with the curing agent of the present invention.

The following examples illustrate the preparation of the hydrazides of the present invention.

EXAMPLE 1

Preparation of

-continued

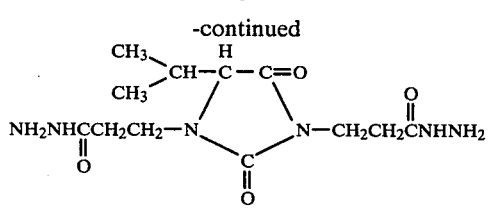

10.0 g of 5-isopropylhydantoin, 50 ml of methyl acrylate, 0.5 g of potassium hydroxide, and 0.5 g of hydroquinone polymerization inhibitor were mixed in a three-necked flask equipped with a stirrer, and the mixture was heated under reflux for 3 hours with stirring. From the reaction mixture, excess methyl acrylate was removed in vacuo and the residue was dissolved in 50 ml of ethyl acetate. After washing three times with 30 ml of water, ethyl acetate was removed to obtain 15.3 g of adduct of 5-isopropylhydantoin and bimolecular methylacrylate.

12.0 g of the adduct thus obtained and 4 ml of hydrazine hydrate were dissolved in 30 ml of ethanol, and the solution was heated under reflux for 4 hours with stirring. From the reaction mixture, excess hydrazine hydrate and ethanol were removed in vacuo.

The residue was dissolved in 20 ml of ethanol and allowed to stand overnight to precipitate the crystals. After filtration, the crystals were washed with ethanol, dried under reduced pressure to obtain 10.3 g of white crystals.

The analytical values were as shown below.
Melting point: 123° to 125° C.

| Elemental analysis | (%) | | |
|---|---|---|---|
| | C | H | N |
| Found | 45.83 | 7.21 | 26.80 |
| Calculated for $C_{12}H_{22}N_4O_6$ | 45.85 | 7.05 | 26.74 |

Field Desorption Mass Spectrum: [M+H]+ at m/z 315.

From the above data and the IR data, these white crystals were confirmed as being the target product. This compound was referred to as sample A.

EXAMPLE 2

Preparation of

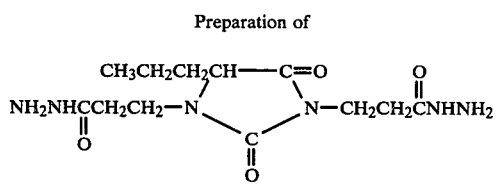

20 g of 5-propylhydantoin, 30 g of methyl acrylate, 0.5 g of potassium hydroxide, and 0.5 g of hydroquinone were mixed in a three-necked flask equipped with a stirrer. According to the method described in Example 1, the mixture was allowed to react to obtain 32.5 g of bimolecular methylacrylate adduct of 5-propylhydantoin. 32.0 g of the adduct thus obtained and 15.5 g of hydrazine hydrate were dissolved in 40 ml of methanol. The solution was crystallized by the same procedure described in Example 1 to obtain 24.5 g of white crystals.

The analytical values were as shown below.
Melting Point: 133° to 135° C.

| Elementary analysis | (%) | | |
|---|---|---|---|
| | C | H | N |
| Found | 45.60 | 7.15 | 26.75 |
| Calculated for $C_{12}H_{22}N_6O_4$ | 45.85 | 7.05 | 26.74 |

Field Desorption Mass Spectrum: [M+H]+ at m/z 315.

From the above data and the IR data, the obtained crystals were confirmed as being the target product. This compound was referred to as sample B.

EXAMPLE 3

Preparation of

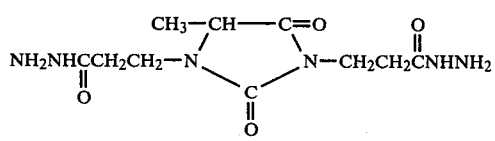

The procedure of Example 1 was repeated except that 22.8 g of 5-methylhydantoin was employed as starting material instead of 5-isopropylhydantoin. There was obtained 30.5 g of white crystals.

The analytical values are shown below.
Melting Point: 164° to 165° C.

| Elemental analysis | (%) | | |
|---|---|---|---|
| | C | H | N |
| Found | 41.85 | 6.43 | 29.25 |
| Calculated for $C_{10}H_{18}N_6O_4$ | 41.95 | 6.34 | 29.36 |

Field Desorption Mass Spectrum: M+ at m/z 286.

From the above data and IR data, the obtained crystals were confirmed as being the target product. This compound was referred to as sample C.

EXAMPLE 4

Preparation of

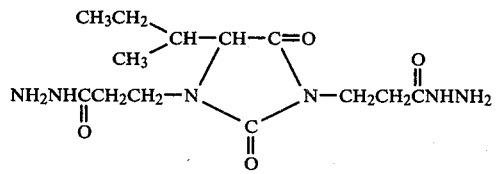

The procedure of Example 1 was repeated except that 5 g of 5-sec.-butylhydantoin was employed as starting material instead of 5-isopropylhydantoin. There was obtained 3.5 g of white crystals.

The analytical values are shown below.
Melting point: 107° C.

| Elemental analysis | (%) | | |
|---|---|---|---|
| | C | H | N |
| Found | 47.40 | 7.42 | 25.85 |
| Calculated for $C_{13}H_{24}N_6O_4$ | 47.55 | 7.37 | 25.60 |

Field Desorption Mass Spectrum: M+ at m/z 328.

From the above data and the IR data, the obtained crystals were confirmed as being the target product. This compound was referred to as sample D.

EXAMPLE 5

Preparation of

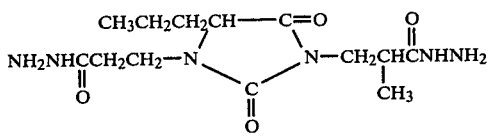

In an autoclave equipped with electromagnetic stirrer, 15 g of 5-propylhydantoin, 31.8 g of methyl methacrylate, 0.4 g of potassium hydroxide, and 0.4 g of hydroquinone were mixed. The mixture was heated to 130° to 140° C. for 5 hours with stirring under atmosphere of nitrogen gas. After cooling, 300 ml of methanol was added to the reaction mixture to precipitate the polymer of methyl methacrylate. Then the polymer was removed by filtration under the reduced pressure, and the filtrate was concentrated and dried. The residue was dissolved in 200 ml of ethyl ether, washed three times with 100 ml of water, and removed ethyl ether to obtain 1.75 g adduct of 5-propylhydantoin and equimolecular methyl methacrylate (mp. 91° to 92° C.).

To 4 g of the adduct of 5-propylhydantoin and methyl acrylate thus obtained, 4 g of methyl acrylate, 0.1 g of potassium hydroxide and 0.1 g of hydroquinone were added. Thereafter, the procedure of Example 1 was repeated to obtain 1.3 g of white crystals.

The analytical values are shown below.
Melting point: 152° to 154° C.

| Elementary analysis | (%) | | |
|---|---|---|---|
| | C | H | N |
| Found | 47.25 | 7.43 | 25.20 |
| Calculated for $C_{13}H_{24}N_6O_4$ | 47.56 | 7.32 | 25.61 |

Field Desorption Mass Spectrum: $M^+$ at m/z 328.

From the above data and the IR data, the obtained crystals were confirmed as being the target product. This compound was referred to as sample E.

EXAMPLE 6

Preparation of

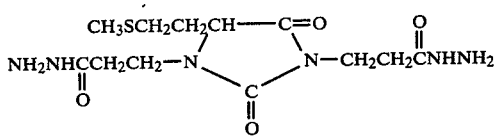

34.8 g (0.2 mole) of methionine hydantoin (5-[2(methyl(thio)ethyl])-hydantoin, 41.3 g (0.48 mole) of methyl acrylate, 0.5 g of sodium hydroxide and 0.5 g of hydroquinone were mixed in a three-necked flask equipped with a stirrer. The mixture was heated under reflux for five hours with stirring. Then, the reaction mixture was dissolved in 200 ml of benzene. After washing twice with 100 ml of water, benzen was removed under the reduced pressure to obtain 58.5 g of methionine hydantoin-bimolecular methyl acrylate adduct (a).

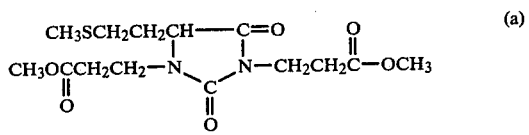

58.5 g of the adduct thus obtained and 25.5 g of 80% aqueous hydrazine hydrate solution were dissolved in 180 ml of methanol and the solution was heated under reflux for four hours with stirring. From this reaction mixture, unreacted hydrazine hydrate and methanol were removed under the reduced pressure, and the residue was dissolved in 50 ml of methanol. After standing overnight, the precipitated crystals were filtered, washed with methanol and dried in vacuo to obtain 33 g of white crystals.

The analytical values are shown below.
Melting Point: 151° C.

| Elemental analysis | (%) | | |
|---|---|---|---|
| | C | H | N |
| Found | 41.80 | 6.66 | 24.17 |
| Calculated for $C_{12}H_{22}N_6O_4S$ | 41.61 | 6.40 | 24.26 |

Field Desorption Mass Spectrum: $[M+H]^+$ at m/z 347.

IR spectrum 3310 cm$^{-1}$, 3270($-NH_2$), 3190, 3150(NH$\overset{O}{\overset{\|}{C}}$)

1755($-CH_2\overset{O}{\overset{\|}{C}}NH$), 1680($\overset{}{\nwarrow}N-\overset{O}{\overset{\|}{C}}-N\overset{}{\swarrow}$)

1610($-NH_2$), 1320($CH_3-S$)

NMR spectrum (heavy water solvent)

δ (ppm)
2.1 (3H, s, $CH_3-S$)
Around 2.3 (2H, m, $CH-CH_2-CH_2$)

Around 2.5 $\begin{pmatrix} 6H, t, CH_2-CH_2-S \\ CH_2-CH_2-CONH \end{pmatrix}$

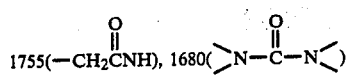

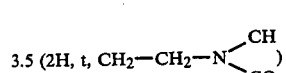

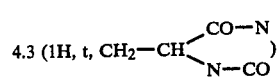

From the above data, the obtained crystals were confirmed as being the target product. This compound was referred to as sample F.

EXAMPLE 7

Preparation of

-continued

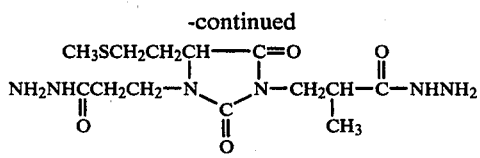

In an autoclave equipped with electromagnetic stirrer, 34.8 g (0.2 mole) of methionine hydantoin, 72 g (0.72 mole) of methyl methacrylate, 0.5 g of potassium hydroxide, and 0.5 g of hydroquinone were mixed. After nitrogen was substituted for air, the mixture was heated for five hours at 150° to 160° C. with stirring. The reaction mixture was dissolved in 300 ml of benzene, and the benzen layer was concentrated. To this solution, 300 ml of methanol was added to precipitate the polymer of methyl methacrylate. After removing the polymer by filtration under the reduced pressure, the filtrate was concentrated and dried to obtain 31.9 g of the adduct of methionine hydantoin and methyl methacrylate.

18.3 g (0.067 mole) of the adduct thus obtained, 17.2 g (0.201 mole) of methyl acrylate, 0.2 g of potassium hydroxide and 0.3 g of hydroquinone were mixed, heated under reflux for 5 hours with stirring. To this reaction mixture, 100 ml of toluene was added, and the solution was washed five times with water. Then toluene removed and 21.5 g of viscous liquid was obtained. To 21.5 g (0.06 mole) of the compound thus obtained, 1.49 g of 80% aqueous hydrazine hydrate solution and 40 ml of ethanol were added, and the mixture was heated under reflux for 4 hours. After removing ethanol and the unreacted hydrazine hydrate from the reaction mixture, 50 ml of 80% aqueous methanol solution was added to precipitate the crystals. The crystals were filtered in vacuo and dried to obtain 11.6 g of white powder.

The analytical values are shown below.
Melting Point: 169° to 171° C.

| Elemental analysis | (%) | | |
|---|---|---|---|
| | C | H | N |
| Found | 43.62 | 6.35 | 23.70 |
| Calculated for $C_{13}H_{24}N_6O_4S$ | 43.33 | 6.67 | 23.33 |

Field Desorption Mass Spectrum: [M+H]+ at m/z 361.

From the above data, the obtained crystals were confirmed as being the target product. This compound was referred to sample G.

EXAMPLE 8

Reactivity and storage stability of the formulated epoxy resin composition were evaluated.

1. Preparation of the sample

The formulation of the sample is shown in Table 1. The sample was stirred for 1 hour with defoaming under the reduced pressure by using the mixing and grinding machine.

2. Evaluation of the reactivity (1) Onset temperature and peak temperature were measured by differential thermal analysis (DTA)
  Sample weight : about 10 mg
  Standard material : $\alpha$-$Al_2O_3$
  Heating rate : 5° C./min.

(2) The sample was put into the Geer's oven maintained to 130° C. and the resulted cure resin was observed on its appearance.

3. Storage stability

The sample was put into the Geer's oven set to 40° C. and the day required for the sample becoming non-fluidity was measured.

TABLE 1

| | Formulation No. | | | | | | | | | |
|---|---|---|---|---|---|---|---|---|---|---|
| | 1 | 2 | 3 | 4 | 5 | 6 | 7 | 8 | 9 | 10 |
| Epon 828 *1) | 100 | 100 | 100 | 100 | 100 | 100 | 100 | 100 | 100 | 100 |
| Sample A | 40 | | | | | | | | | |
| Sample B | | 40 | | | | | | | | |
| Sample C | | | 37 | | | | | | | |
| Sample D | | | | 43 | | | | | | |
| Sample E | | | | | 42 | | | | | |
| Sample F | | | | | | 46 | | | | |
| Sample G | | | | | | | 47 | | | |
| Adipic dihydrazide | | | | | | | | 23 | | |
| Isophthalic dihydrazide | | | | | | | | | 26 | |
| Dicyandiamide | | | | | | | | | | 8 |

TABLE 2

| | Item | | | |
|---|---|---|---|---|
| | Reactivity | | | |
| Formulation No. | Onset temp. (°C.) | Peak temp. (°C.) | Appearance of the sample (130° C./hr) | Storage stability (40° C.) |
| No. 1 | 96 | 140 | Stiff and transparent material | > 3 weeks |
| 2 | 118 | 150 | Stiff and transparent material | " |
| 3 | 124 | 158 | Stiff and transparent material | " |
| 4 | 100 | 145 | Stiff and transparent material | " |
| 5 | 103 | 154 | Stiff and transparent material | " |
| 6 | 133 | 148 | Stiff and transparent material | " |
| 7 | 142 | 160 | Stiff and transparent material | " |
| 8 | 151 | 171 | not cured | " |
| 9 | 158 | 192 | " | " |
| 10 | 160 | 199 | " | " |

The result of Table 2 shows that the latent curing agent for epoxy resin in this invention has excellent storage stability and reactivity.

Especially, the reactivity of this agent is superior to the control agent.

What we claim is:

1. A method of curing epoxy resin compositions, which comprises:

heating an epoxy resin composition comprising (a) an epoxy resin having an average of more than one epoxy group per molecule and (b) a curing agent comprising a compound having the formula:

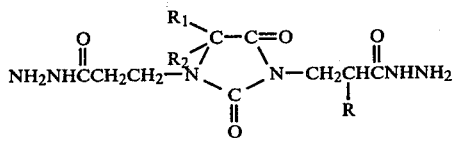

wherein $R_1$ and $R_2$ are each a hydrocarbon atom, $C_1$–$C_8$ alkyl radical or —$CH_2CH_2SCH_3$ radical and R is a hydrogen atom or methyl radical.

2. The method of claim 1, wherein $R_1$ is a hydrogen atom, $R_2$ is methyl, n-propyl, isopropyl, sec.-butyl or —$CH_2CH_2SCH_3$, and R is a hydrogen atom or methyl radical.

3. A curable epoxy resin composition comprising (a) an epoxy resin having an average of more than one epoxy group per molecule and (b) a curing agent comprising a compound having the formula:

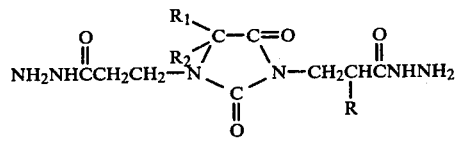

wherein $R_1$ and $R_2$ are each a hydrogen atom, $C_1$–$C_8$ alkyl radical or —$CH_2CH_2SCH_3$ radical, and are the same or different from each other; and R is a hydrogen atom or methyl radical.

4. The curable epoxy resin composition claimed in claim 3, wherein the amount of said compound is sufficient to provide 0.5–1.5 times active hydrogen equivalent weight based on epoxy equivalent weight.

5. The curable epoxy resin composition claimed in claim 3, wherein $R_1$ is a hydrogen atom, $R_2$ is methyl, propyl, isopropyl, sec.-butyl or —$CH_2CH_2SCH_3$, and R is a hydrogen atom or methyl radical.

6. The curable epoxy resin composition claimed in claim 3, wherein said epoxy resin is a polyglycidyl ether of a polyhydric phenol.

7. A cured resin obtained by contacting an epoxy resin having an average of more than 1 epoxy group per molecule with a curing agent comprising a compound having the formula:

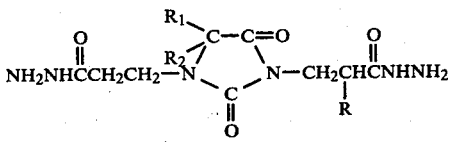

wherein $R_1$ and $R_2$ are each a hydrogen atom, $C_1$–$C_8$ alkyl radical or —$CH_2CH_2SCH_3$ radical, and are the same or different from each other; and R is a hydrogen atom or methyl radical, the amount of said compound being sufficient to provide 0.5–1.5 times active hydrogen equivalent weight based on epoxy equivalent weight.

8. The curable epoxy resin composition claimed in claim 5, wherein the amount of said compound is sufficient to provide 0.5–1.5 times active hydrogen equivalent weight per epoxy equivalent weight.

9. The curable epoxy resin composition claimed in claim 8, wherein the amount of said compound is sufficient to provide 0.7–1.2 times active hydrogen equivalent weight per epoxy equivalent weight.

10. The curable epoxy resin composition claimed in claim 3, wherein said epoxy resin is a glycidyl ether of a polyhydric phenol wherein the polyhydric phenol is selected from the group consisting of 2,2-bis(4-hydroxyphenyl)-propane, resorcinol, hydroquinone, pyrocatechol, salignenin, Bisphenol F and phenolformaldehyde resin.

11. The cured resin claimed in claim 7, wherein the amount of said compound is sufficient to provide 0.7–1.2 times active hydrogen equivalent weight per epoxy equivalent weight.

12. The method of claim 1, wherein said heating is in the range of from 100° to 130° C.

* * * * *